(12) United States Patent
Jin

(10) Patent No.: US 11,000,078 B2
(45) Date of Patent: May 11, 2021

(54) PERSONAL AIRBAG DEVICE FOR PREVENTING BODILY INJURY

(71) Applicant: Xin Jin, Waterloo (CA)

(72) Inventor: Xin Jin, Waterloo (CA)

( * ) Notice: Subject to any disclaimer, the term of this patent is extended or adjusted under 35 U.S.C. 154(b) by 212 days.

(21) Appl. No.: 16/184,070

(22) Filed: Nov. 8, 2018

(65) Prior Publication Data

US 2019/0110530 A1    Apr. 18, 2019

Related U.S. Application Data

(63) Continuation-in-part of application No. 14/980,001, filed on Dec. 28, 2015, now Pat. No. 10,154,695.

(51) Int. Cl.
| | | |
|---|---|---|
| *A41D 13/018* | (2006.01) | |
| *A61B 5/11* | (2006.01) | |
| *A41D 13/015* | (2006.01) | |
| *G01P 13/00* | (2006.01) | |
| *A41D 1/00* | (2018.01) | |
| *G01P 15/08* | (2006.01) | |

(52) U.S. Cl.
CPC ......... *A41D 13/0155* (2013.01); *A41D 1/002* (2013.01); *A41D 13/018* (2013.01); *A61B 5/1117* (2013.01); *G01P 13/00* (2013.01); *G01P 15/0891* (2013.01)

(58) Field of Classification Search
CPC ................ A41D 13/018; A61B 5/1117; G05B 19/0428; G08B 21/0476; A62B 99/00
USPC ........................................................ 182/137
See application file for complete search history.

(56) References Cited

U.S. PATENT DOCUMENTS

| | | | | |
|---|---|---|---|---|
| 5,052,065 A | * | 10/1991 | West .................. | A61G 5/10 5/424 |
| 5,500,952 A | * | 3/1996 | Keyes ................ | A41D 13/018 2/465 |
| 5,592,705 A | * | 1/1997 | West .................. | A47C 21/08 182/137 |
| 6,594,835 B2 | * | 7/2003 | West .................. | A47C 21/00 182/137 |
| 7,420,472 B2 | * | 9/2008 | Tran .................. | G16H 20/60 340/573.1 |
| 7,502,498 B2 | * | 3/2009 | Wen .................. | G06K 9/00221 382/128 |
| 9,047,751 B2 | * | 6/2015 | Yamamoto ......... | G06K 9/00369 |
| 9,247,211 B2 | * | 1/2016 | Zhang ............... | H04N 7/181 |
| 9,472,082 B2 | * | 10/2016 | DeLean ............. | G08B 5/002 |
| 9,489,730 B2 | * | 11/2016 | Doettling ........... | G06T 7/0004 |
| 9,568,594 B2 | * | 2/2017 | Harash .............. | G01S 13/886 |
| 10,007,850 B2 | * | 6/2018 | Leung ............... | G06K 9/00771 |
| 10,424,180 B2 | * | 9/2019 | Tang ................. | G06T 7/13 |

(Continued)

FOREIGN PATENT DOCUMENTS

| | | | | | |
|---|---|---|---|---|---|
| CA | | 2862088 A1 | * | 8/2012 | ........... A61B 5/1117 |
| FR | | 2954988 A1 | * | 7/2011 | ........... A61B 5/1126 |

(Continued)

*Primary Examiner* — Ruth Ilan

(57) ABSTRACT

For people with reduced physical ability such as elderly people, risks of bodily injuries are high. Once an injury occurs, a victim suffers, sometimes a victim even may not survive. To help such people, a device without adding much inconvenience in normal life is disclosed. The device is able to detect dangerous conditions and automatically deploy airbags when needed to prevent or mitigate potential bodily injuries.

20 Claims, 8 Drawing Sheets

(56) References Cited

U.S. PATENT DOCUMENTS

| | | | | |
|---|---|---|---|---|
| 10,539,941 B2* | 1/2020 | Hyde | | A41D 13/05 |
| 10,572,723 B2* | 2/2020 | Jiang | | A61B 5/1123 |
| 2003/0058341 A1* | 3/2003 | Brodsky | | G08B 21/043 |
| | | | | 348/169 |
| 2004/0003455 A1* | 1/2004 | Davidson | | A61F 5/028 |
| | | | | 2/455 |
| 2006/0001545 A1* | 1/2006 | Wolf | | G08B 21/0461 |
| | | | | 340/573.1 |
| 2006/0049950 A1* | 3/2006 | Lockhart | | A61B 5/1117 |
| | | | | 340/573.1 |
| 2006/0241521 A1* | 10/2006 | Cohen | | A61B 5/1112 |
| | | | | 600/595 |
| 2009/0254003 A1* | 10/2009 | Buckman | | A61B 5/1117 |
| | | | | 600/595 |
| 2010/0004567 A1* | 1/2010 | Ishikawa | | A61B 5/6807 |
| | | | | 600/595 |
| 2010/0316253 A1* | 12/2010 | Yang | | G08B 21/0453 |
| | | | | 382/103 |
| 2012/0131718 A1* | 5/2012 | Uchida | | A41D 13/018 |
| | | | | 2/69 |
| 2013/0326800 A1* | 12/2013 | Kim | | A41D 13/05 |
| | | | | 2/455 |
| 2014/0047623 A1* | 2/2014 | Richards | | A62B 35/00 |
| | | | | 2/455 |
| 2014/0123374 A1* | 5/2014 | Gelston | | A41D 13/018 |
| | | | | 2/455 |
| 2014/0244037 A1* | 8/2014 | Scott | | G06K 9/228 |
| | | | | 700/253 |
| 2015/0101112 A1* | 4/2015 | Balbien | | A41D 13/0512 |
| | | | | 2/465 |
| 2015/0269825 A1* | 9/2015 | Tran | | A61B 5/4806 |
| | | | | 340/539.12 |
| 2016/0120238 A1* | 5/2016 | Duncan | | A41D 13/018 |
| | | | | 2/462 |
| 2016/0174626 A1* | 6/2016 | Mazzarolo | | A41D 13/018 |
| | | | | 2/455 |
| 2016/0183607 A1* | 6/2016 | Lopez Yunez | | A41D 13/018 |
| | | | | 2/455 |
| 2016/0213072 A1* | 7/2016 | Chung | | A41D 13/018 |
| 2016/0375970 A1* | 12/2016 | Johnston | | B63C 9/155 |
| | | | | 2/463 |
| 2017/0006931 A1* | 1/2017 | Guez | | A41D 13/018 |
| 2017/0140631 A1* | 5/2017 | Pietrocola | | G08B 31/00 |
| 2017/0181485 A1* | 6/2017 | Jin | | A41F 9/002 |
| 2017/0208874 A1* | 7/2017 | Davenport | | A41D 1/002 |
| 2017/0224031 A1* | 8/2017 | Raanan | | A41D 13/0506 |
| 2017/0277158 A1* | 9/2017 | Hyde | | A41D 13/05 |
| 2017/0281056 A1* | 10/2017 | Raanan | | A61B 5/6831 |
| 2018/0174320 A1* | 6/2018 | Hayashi | | G06K 9/00342 |
| 2018/0284223 A1* | 10/2018 | Otsuki | | G01S 13/003 |
| 2019/0099113 A1* | 4/2019 | Roder | | A61B 5/7275 |
| 2019/0188815 A1* | 6/2019 | Ananthapur Bache | | |
| | | | | G06Q 50/265 |
| 2019/0357618 A1* | 11/2019 | Zheng | | G08B 21/043 |
| 2019/0385322 A1* | 12/2019 | Gu | | G06T 7/60 |
| 2020/0143656 A1* | 5/2020 | Li | | G08B 21/043 |

FOREIGN PATENT DOCUMENTS

| | | | | |
|---|---|---|---|---|
| WO | WO-2011016782 A1 * | 2/2011 | | A61B 5/0059 |
| WO | WO-2015183470 A2 * | 12/2015 | | A41D 13/02 |

* cited by examiner

PERSONAL AIRBAG DEVICE FOR PREVENTING BODILY INJURY

CROSS-REFERENCE TO RELATED APPLICATION

This application is a continuation-in-part of U.S. application Ser. No. 14/980,001, filed on Dec. 28, 2015.

BACKGROUND OF THE INVENTION

Field of the Invention

This invention relates generally to device to prevent bodily injury, in particular, to an airbag device and its control method to prevent bodily injury caused by impacts such as falling down, or being hit by high speed blunt objects.

Description of the Related Art

Airbags have been widely used in automobiles to prevent injury in vehicle collision accidents. An airbag inflates when a collision is detected by a control unit through various sensors installed on vehicle (e.g., accelerometers, impact sensors, side door pressure sensors, wheel speed sensors, gyroscopes, brake pressure sensors, and seat occupancy sensors), creating a cushion between a driver/passenger and other hard objects on the vehicle, reducing the risk of severe bodily injury.

Wearable devices such as helmets, armors, bulletproof vests, and kneepads may be used to protect particular parts of body from injury when a person is performing specific tasks. Particular groups of people such as elderly people, handicapped persons, construction site workers experience higher risks of bodily injury than many others, on the other hand, wearing armors and helmets all time is inconvenient for them. There is a need in the art to smartly deploy a protection against injury when needed while minimizing the inconvenience caused by wearable protection devices.

Reliably detecting falling of a person that is likely causing bodily injury before the falling person hitting ground and/or other object is more challenging a task than detecting a person had felled after the fact. Timely detection of an on-going falling of a person would make it possible to take injury prevention actions before injury occurs, e.g., inflating an airbag to prevent or reduce severity of potential injury. There is a need in the art to develop method and system to reliably and timely detect an on-going falling of a person and to prevent bodily injury of the person.

BRIEF SUMMARY OF THE INVENTION

In one aspect, the invention provides an airbag device for preventing bodily injury of a user, comprising: at least one inflatable airbag, mounted on the airbag device for absorbing energy when the user is falling and hits the floor or an object, at least one airbag inflator, for accepting an igniting signal to inflate the at least one inflatable airbag, at least one image sensor, for taking images in real-time of body segments of the user and objects surrounding the user, and a controller, coupled with the at least one airbag inflator, and the at least one image sensor, whereby the controller is operable to determine a status indicating whether the user is falling based, at last in part, on information extracted from the images, make a decision of airbag inflation based, at least in part, on the determined status of falling, and send an igniting signal to the at least one airbag inflator upon positive decision of airbag inflation.

In another aspect, at least one embodiment of the invention provides an airbag device for preventing bodily injury of a user, wherein the controller of the airbag device is operable to determine whether or not to inflate the airbag through at least one of intermediate steps in determining: relative positions in 3-dimensions of body segments of the user, based, at least in part, on information extracted from images and constraints of connections between the segments, relative positions in 3-dimensions of center of mass of each of the body segments of the user, based, at least in part, on information extracted from the images; a relative position of overall center of mass of the user body, based, at least in part, on relative positions of the center of mass and weights of each of the body segments of the user; a relative position of overall center of mass of the user body, based, at least in part, on geometry center of the overall user body or geometry center of each of the body segments of the user, a status indicating the user is sitting or standing, based, at least in part, on information extracted from the images, a relative position of supporting base footprint, based on relative positions of feet when determined standing, and based on relative positions of feet and buttock when determined sitting, and a status indicating whether the user is falling based, at least in part, on relative position of an overall center of mass of the user body, relative position of the supporting base footprint, and a direction of the gravity.

In yet another aspect, the invention provides an airbag protection system for preventing bodily injury of a user, comprising: at least one mobile platform that moves accompanying with the user, at least one inflatable airbag device, stored on the at least one mobile platform, for being deployed and inflated on floor and absorbing impact energy when the user falls towards floor, at least one airbag device launcher, mounted on the at least one mobile platform, for popping out on floor the inflatable airbag device, at least one airbag inflator, for accepting an igniting signal to inflate the at least one inflatable airbag device, at least one image sensor, installed on the mobile platform or attached to the user, for taking images of body segments of the user and objects surrounding the user in real-time, and a controller, coupled with the at least one airbag device launcher, the at least one airbag inflator, and the at least one image sensor, whereby the controller is operable to determine a status indicating whether the user is falling based, at last in part, on information extracted from real-time images of the user, send launching signals to the at least one airbag device launcher, and the igniting signal to an airbag inflator associated with the inflatable airbag device being lunched.

Other aspects of the invention will become clear thereafter in the detailed description of the preferred embodiments and the claims.

BRIEF DESCRIPTION OF THE DRAWINGS

For a better understanding of the invention and to show more clearly how it may be carried into effect, reference will now be made, by way of example only, to the accompanying drawings which show at least one exemplary embodiment of the invention and in which.

DETAILED DESCRIPTION OF THE INVENTION

It will be appreciated that in the description herein, numerous specific details are set forth in order to provide a thorough understanding of the invention. However, it will be understood by those of ordinary skill in the art that the invention may be practiced without these specific details. In other instances, well-known methods, procedures and components have not been described in detail so as not to obscure the invention. Furthermore, this description is not to be considered as limiting the scope of the invention, but rather as merely providing a particular preferred working embodiment thereof.

Figure 1:
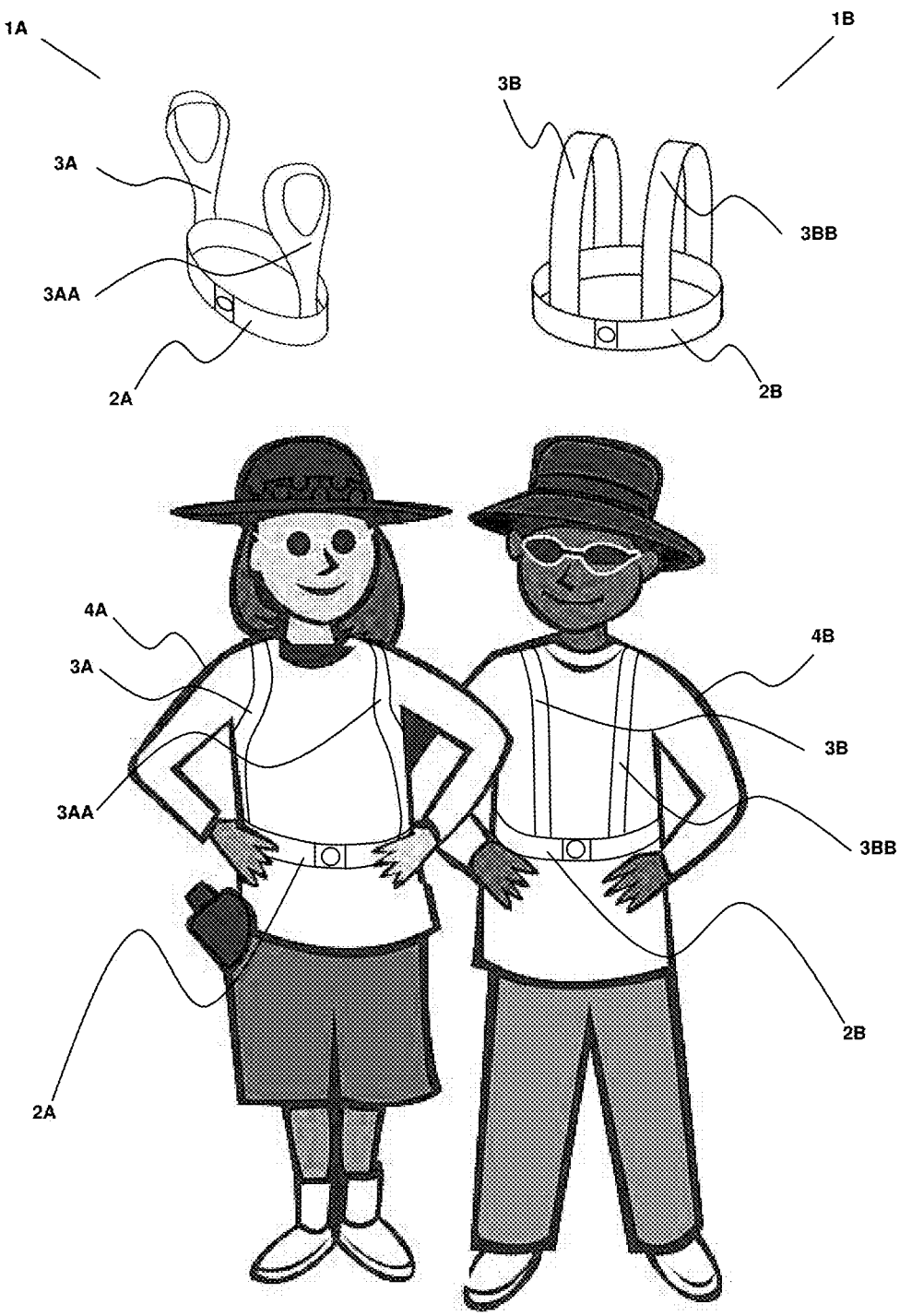
FIG. 1 illustrates a physical look of two exemplary embodiments of wearable airbag devices, when the airbag is not inflated.

FIG. 1 illustrates a physical look of two exemplary embodiments of wearable airbag devices, when the airbag is not inflated. In the embodiments, the airbag device 1A, 1B comprises a waist belt 2A, 2B and shoulder belts 3A, 3AA, 3B, 3BB. In the figure, use cases that users 4A, 4B wear the airbag devices are also illustrated. The shoulder belts 3A, 3AA, 3B, 3BB firmly connect the waist belt 2A, 2B, as shown. Preferably the belts are semi-flexible and durable, with adjustable length to fit a user body, and adapted to the shape of the body. Components of the airbag devices (to be described hereinafter) are embedded into the waist belt 2A, 2B and/or shoulder belts 3A, 3AA, 3B, 3BB. The device is preferably self contained and wearable on the upper body outside other clothing, and is suitable for all season use.

Figure 2:
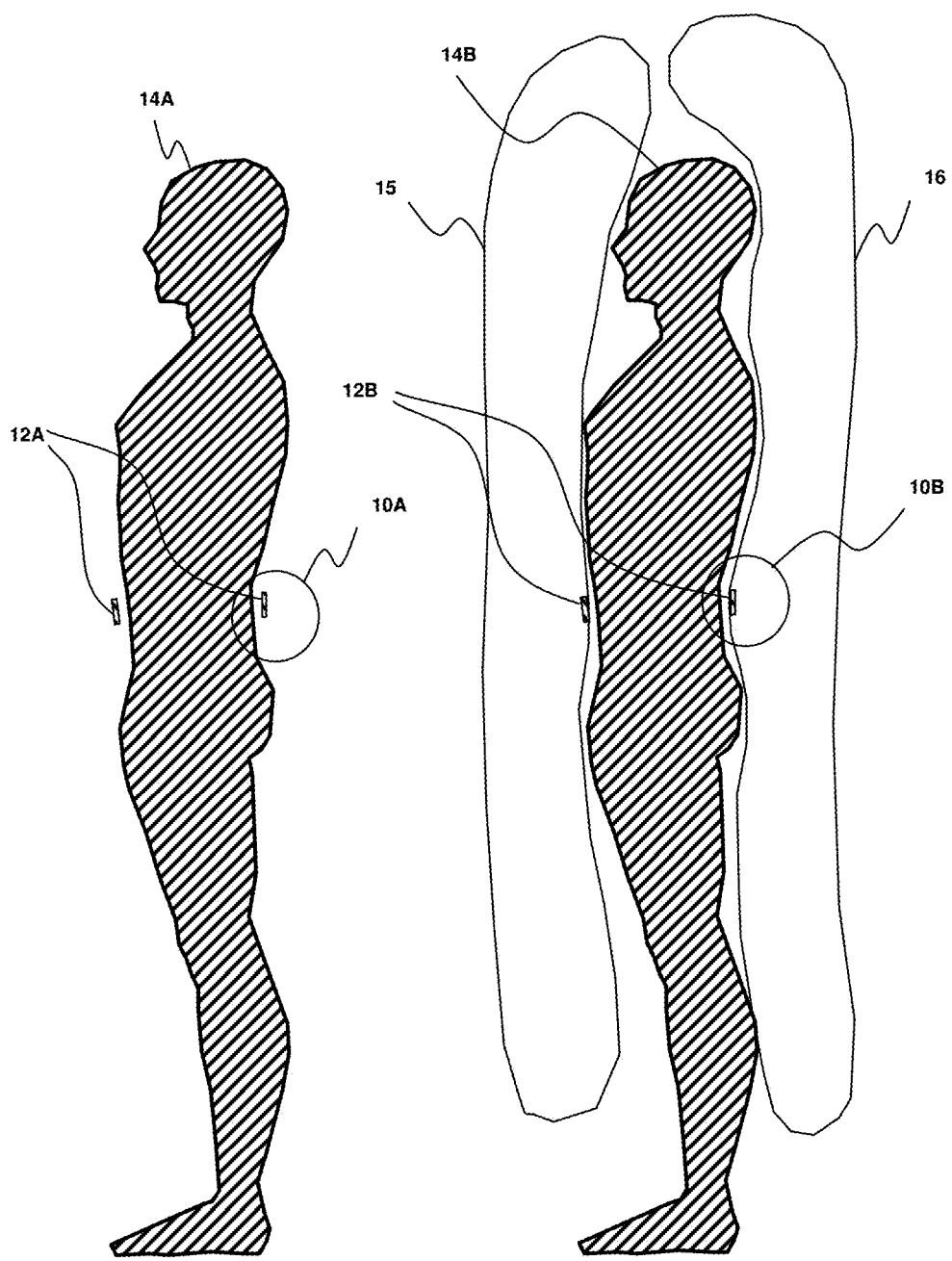
FIG. 2 illustrates sectional views of an exemplary embodiment of wearable airbag device before and after inflation.

FIG. 2 illustrates sectional views of the exemplary embodiment of wearable airbag device before and after inflation. Before inflating, the airbag device 12A is worn on user 14A outside regular clothing (not shown) of the user 14A (note that in the particular sectional view, only the waist belt 12A of the airbag device is shown). The device 12A is a merely a minor add-on accessory that the user 14A wears with minimal inconvenience to the user. When needed, at least one airbags 15, 16 are inflated from the airbag device 12B to protect various parts of the user body 14B. In the example of the embodiment in FIG. 2, one front airbag 15 and one rear airbag 16 are inflated to protect front and rear sides of the user body, respectively. Detailed views of 10A and 10B portions will be described hereinafter in FIG. 3.

Airbag inflation is a very rapid process that generates large amount of gas through, for example, chemical reactions of propellants. Before inflation the airbags are folded in small size and packed, for example, on the wearable belts. The container of propellants may be mounted on the outer side of the belts and wrapped inside the packed airbag. When inflation is initiated, an impact force may be applied backward on the belt. To reduce the pressure and pressure density toward the user body, the belt needs to be built with semi-flexible, durable and thermal resistant material that would distribute the pressure evenly through the inner surface of the belt to the user body without excessive temperature increase on its inner surface. To further reduce the impact under the belt towards user body, a few techniques can be used as will be discussed next.

Figure 3:
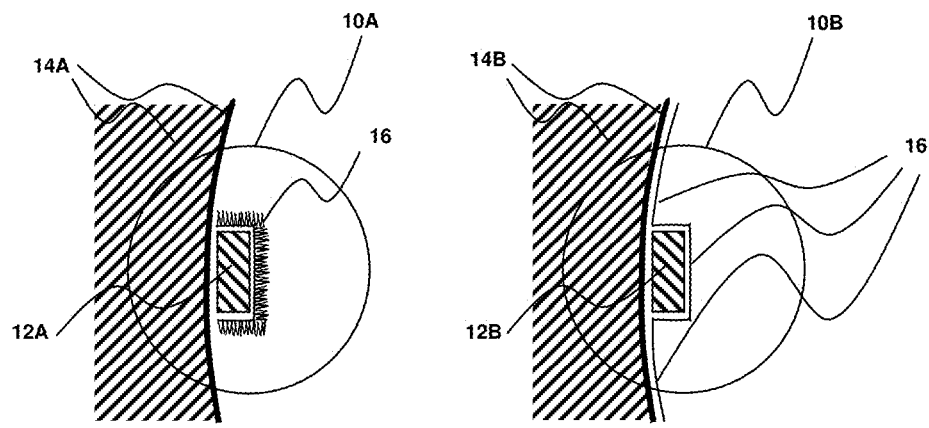
FIG. 3 shows detailed views of 10A and 10B portions of FIG. 2 in a preferred embodiment.

FIG. 3 shows detailed views of 10A and 10B portions of FIG. 2 in a preferred embodiment. When the airbag is not inflated 10A, the airbag 16 is folded around the belt 12A, ready to be inflated, as shown in FIG. 3 10A (not shown in FIG. 2 due to drawing scale). During and after inflation 10B, the airbag 16 preferably deploys and maintains a flat shape with the belt 12B on the user body side, adapted to the surface shape of the body 14B, so that pressure would evenly distributed to the body 14B under both the belt 12B and the bag 16, rather than creating excessively stronger impact under the area of the belt 12B.

Figure 4:
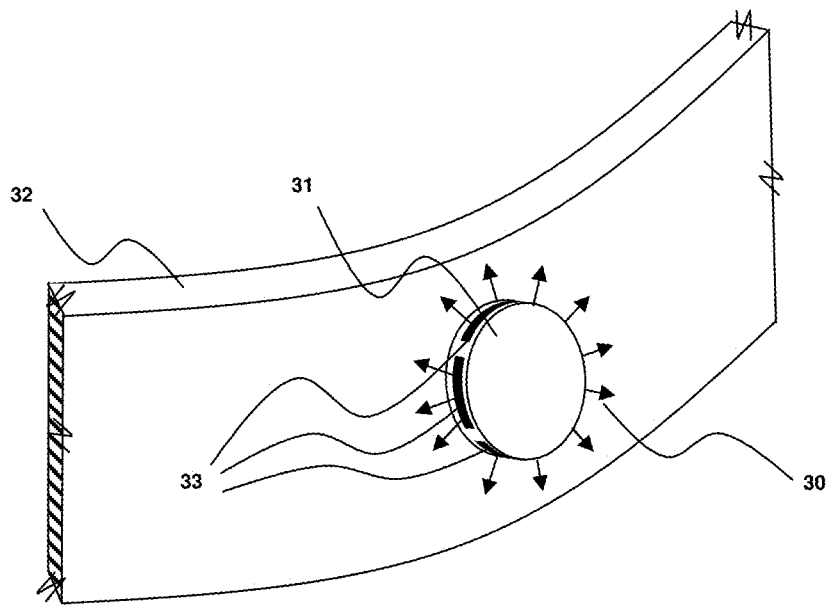
FIG. 4 illustrates a preferred embodiment of an emitter of an airbag inflator.

FIG. 4 illustrates a preferred embodiment of an emitter of an airbag inflator, to achieve better results in distributing the pressure, and avoid excessive impact under the belt. An inflator emitter 31 which may be based on propellant chemical reactions is mounted on the outer side of the belt 32 inside an airbag (airbag is not shown in drawing). The opposite side of the belt faces the user body (not shown in drawing). When the inflator emits gas to the airbag, an impact will be generated in an opposite direction of the gas jet. To avoid strong impact toward user body, the jet emitting directions (marked as arrows 30 in drawing) is designed not towards outside, but in a plane parallel (or almost parallel) to the surface of the belt 32, furthermore, the design makes the jet emitting strength at opposite directions identical or at least nearly identical, so that their impacts cancel each other. To achieve this, the shape of the inflation emitter 31 is preferably symmetric in geometry and the jet emitting holes 33 on the emitter 31 are preferably symmetric about the geometrical center of the emitter 31 in all sectional planes parallel to the mounting surface of belt 32. Besides, jets should be distributed to the emitting holes simultaneously and evenly by design, for example, if the inflator is propellant based, the chemical reaction of propellants needs to take place evenly about the geometrical center of the emitter 31.

Figure 5:
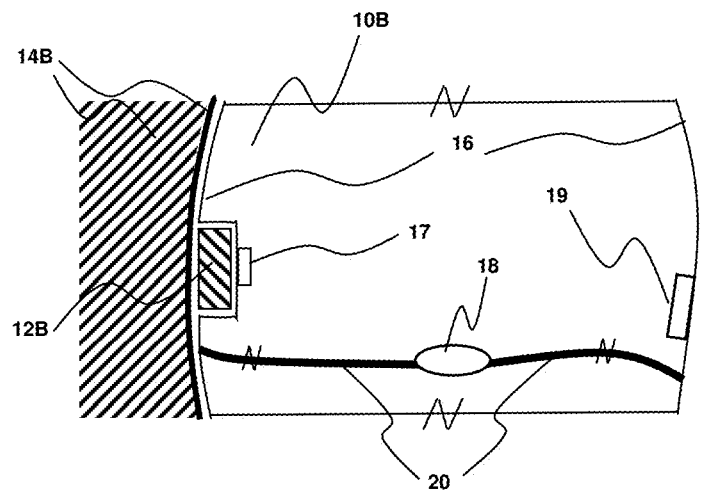
FIG. 5 shows a sectional view of exemplary two-stage inflation embodiments.

In an alternative embodiment, as shown in a partial sectional view in FIG. 5, the airbag 16 may be inflated in two (or more than two) stages. The first stage triggers an inflation emitter 17 mounted on the belt 12B and in turn against user body 14B. During inflation, in order to reduce an impact towards user body 14B under the area of belt 12B, the first stage inflation emitter 17 has relatively small scale, preferably just enough to expand the packed airbag to form its shape. The first stage inflation also pulls additional emitters 18, 19 away from the belt 12B, e.g., pulls the emitter 18 to the middle of the partially inflated airbag 16 by strings (or compartment fabric) 20 tied on both inner and outer sides of the bag 16, or pulls out the emitter 19 that is attached to the outer fabric of the airbag 16; and then, in the second stage of inflation, the emitter 18 in the middle of airbag and/or the emitter 19 attached on the outer fabric of airbag 16 may be ignited, and get the airbag 16 fully inflated. During the second stage of inflation, the emitters 18, 19 are not mounted on the belt 12B, and are preferably designed to emit gas towards opposite directions simultaneously (to avoid the emitter "flies" away by jets). The impact towards user body by the second stage of inflation will be evenly distributed through the entire bag surfaces on the user body side.

Figure 6:
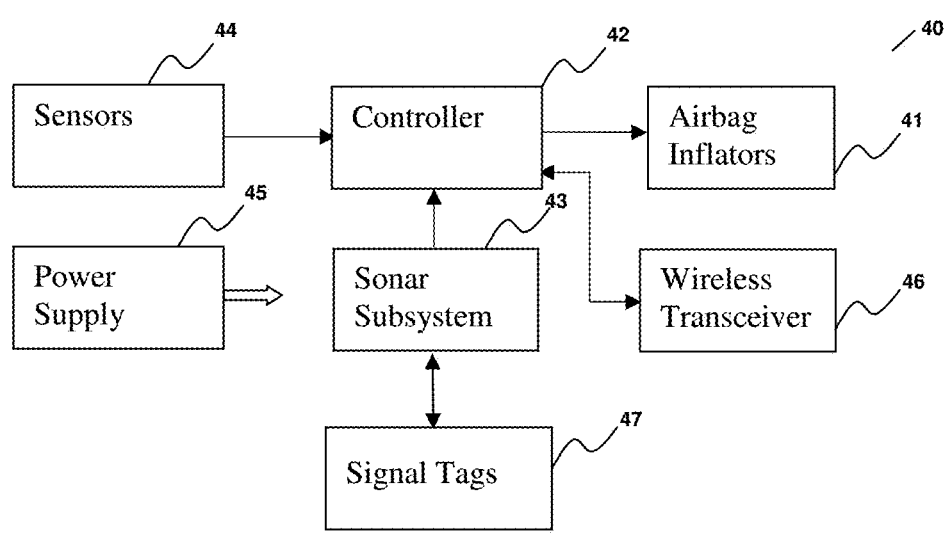
FIG. 6 illustrates a block diagram of an exemplary embodiment of the control system of the wearable airbag device.

FIG. 6 illustrates a block diagram of an exemplary embodiment of the control system 40 of the wearable airbag device. The airbag device is equipped with at least one airbag. In the embodiment shown in FIG. 2, the airbag device is equipped with two airbags, one front bag, and one rear bag. The airbag device may be equipped with multiple airbags, e.g., some airbags to protect the head, some to protect the knee and legs, some to protect the buttock, some to protect the back, some to protect the chest, and some to protect the arms, depending on the protection needs. When more than one airbags are installed, each of them may be controlled to inflate individually, which includes inflating multiple airbags together, one after another, or one airbag alone, depending on the detected risk type by the control system 40. Each individual airbag may be triggered to be inflated by a single inflating device, and may also be triggered to be inflated by more than one inflating devices, depending on the size of the airbag, also depending on other design considerations such as inflating time, acceptable pressure density of the body caused by inflation, and so on. The block of "airbag inflators" 41 in FIG. 6 represents the at least one devices to accept triggering signals (i.e., igniting signals) to activate the inflation of the at least one airbags. An inflator may be designed in separately more than one parts, e.g., an igniter and an emitter, and may also be designed to combine more than one functions in one single part.

The controller 42 is a subsystem that may include at least one microprocessors and signal processors with supporting devices such as memory, clock generation, interfaces to peripheral devices and user, and power management. The controller 42 controls the overall operation of the airbag device (e.g., 1A, 1B in FIG. 1) including the control system 40. Preferably the controller 42 is efficient in energy consumption while providing sufficient processing speed when needed—capable of detecting dangerous conditions and triggering inflation of airbags in the order of milliseconds.

The sonar subsystem 43 is used for detecting dangerous objects that may hit any protected parts of the body, and send the detected information to the controller 42 for further processing. An object is dangerous to a protected part of the user body if the object and the protected part of the user body are getting closer with a speed higher than a safe speed, and with a distance lower than a safe distance. The sonar subsystem 43 preferably is able detect the relative velocity and distance between a surrounding object and the protected portion of the user body in real-time. In a preferred embodiment, the sonar subsystem 43 is based on ultrasound signals. Ultrasound signal is superior to radio signal (electromagnetic signal) for detecting objects that may hit the user because many solid objects that may hurt the body does not reflect radio signals, or reflects little. A radio signal based detector (radar) may not be able to detect such objects. Ultrasound can be reflected by almost all solid object surfaces. Also, in a preferred embodiment, Doppler effect is used by the sonar subsystem to detect the relative velocity between an object and the user body. This gives another reason that ultrasound is superior to radio signal for the detection, because the radio signal propagates at very high speed, relative movements of a surrounding object in a regular user's daily life only cause very small amount of Doppler shift, but ultrasound has much lower propagation speed than radio signals, the Doppler shift would be much more significant, and easier to detect. Preferably the sonar subsystem is implemented to be able to detect and measure both relative velocity and distance, and optionally is further able to detect and measure acceleration/deceleration.

The airbag devices may further include various sensors 44 deployed at various positions of the airbag device (e.g., 1A, 1B in FIG. 1) and/or various positions on the user body (not shown in drawings) that are coupled with the controller 42, such as accelerometers (gravimeters), gyro sensors (gyroscope sensors), muscle electrical potential sensors, pressure sensors, microphone or other types of vibration sensor, infrared and image sensors, cameras, video cameras, etc. In one embodiment, the sensors are used to detect the user mode of activity, sometimes referred to as posture mode detection. For example, when detected that a user is sitting (usually this posture has relatively low risk), all devices 40 can enter a mode of operation that reduces energy consumption, to increase battery life of the airbag device. This energy saving mode can be achieved, for example, by reducing the clock rate of the processors in the controller 42, or by periodically putting the processors and devices in an energy saving "sleep" mode. Detecting the user is walking smoothly, for example, the controller 42 may decide to change the mode of operation to a moderate energy consumption rate, because the risk level is moderately high. Detecting the user is in a transition of his/her activity, such as from sitting to standing-up, from standing to walking, from walking straight to making a turn, suddenly stopping walking, etc., these transition periods usually have higher risks and the controller may switch the control system devices 40 to a mode providing highest performance with highest energy consumption. In an alternative embodiment, the sensors provide information for the controller 42 for making a decision of airbag inflation in addition to or jointly with the information provided by the sonar subsystem, to increase the level of confidence and reduce false alarms and/or missed detections of dangerous conditions. For example, when a user falls down, accelerometers and/or gyro sensors deployed at upper user body may provide information to the controller to detect the falling condition either solely based on the sensor information, or jointly with sonar detected information; while falling, a user would commonly feel nervous and his/her arms may try to reach the ground to support his/her body, muscle electrical potential sensors may detect such user action and provide the detected information to the controller 42 for a decision of airbag inflation. When a pressure sensor embedded in shoes detecting a foot is on floor but a microphone or image or infrared sensor on the shoe detects the foot is still moving (through frictional noise and/or moving images), it is an indication of slipping, the information can be fed to the controller 42 for decision making of airbag inflation. Image sensors such as still picture cameras or video cameras may take images of the user movement in real-time and based on images to extract the information to detect dangerous conditions to control the airbag inflation, more details will be described thereinafter. Cameras may also record situations through still images and/or videos during events of the airbag inflations for event analysis purpose. Some sensors may also be used by a 3D body posture determination method that will be described in detail hereinafter.

The power supply unit 45 is responsible for providing power to all subsystems of the control system 40. In a preferred embodiment the power supply unit supports two sets of independent detachable batteries (not shown), and either of the two sets of batteries is able to support the full operation of the airbag control system 40. Preferably the batteries are hot swappable, i.e., any one of the batteries can be replaced while the other battery is automatically on duty without affecting the functionality of the airbag device. The power supply unit will control the use of the two sets of batteries smartly and providing indication which battery needs to be replaced, e.g., for charging offline. When a user is by mistake attempting to replace a wrong battery that is currently powering the airbag device while the other one is depleted, preferably the active battery is automatically locked and not detachable by user.

The control system 40 of the airbag device may further include a wireless transceiver subsystem 46 that is used to report incidents of airbag inflations. The reports may be received by a service center to dispatch service staff to the user in the event of airbag inflation. Through the wireless transceiver 46, service staff may also speak to the user and/or surrounding people at the user's location to provide guidance to handle situations in an airbag inflation event. Event logging data may also be transmitted to service center through the wireless transceiver 46. Software upgrades may also be downloaded onto the control system 40 through the wireless transceiver 46. Besides, some sensors (in the block 44) may also be coupled to the controller 42 via wireless transceiver 46. The block of wireless transceiver may including more than one wireless air interface technologies, and may also further include global positioning satellite receivers (GPS, GLONASS, Beidou, Galileo and the like) for obtaining user location information. The wireless transceiver 46 may also be used to transfer data and signaling among subsystems and sensors of the control system 40.

The control system 40 of the airbag device may further include a number of signal tags 47 placed at various locations on the user body, for detecting a falling condition of the user. This feature is explained in detail hereinafter with FIG. 9.

Figure 7:
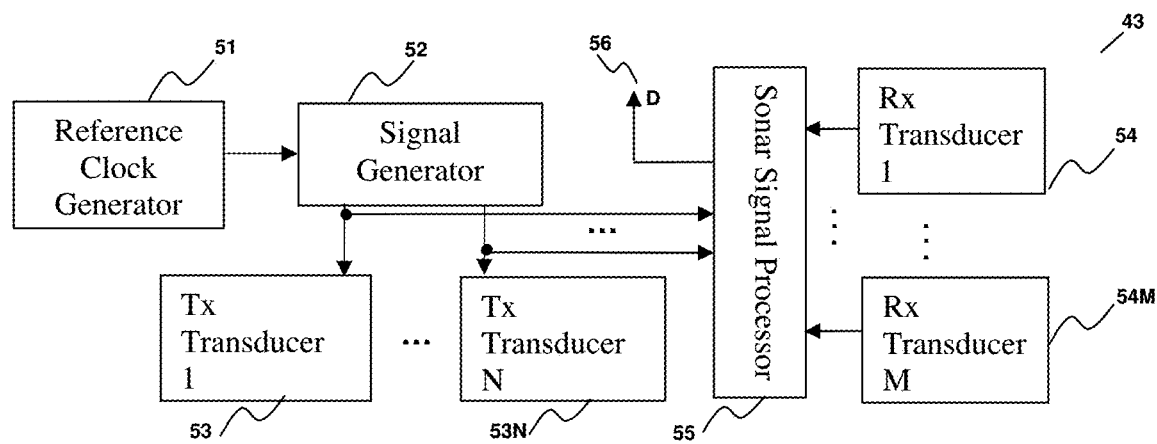
FIG. 7 is an exemplary embodiment of the sonar subsystem presented in a more detailed functional block diagram.

FIG. 7 is an exemplary embodiment of the sonar subsystem 43 presented in a more detailed functional block diagram. In order to detect dangerous conditions around all protected parts of user body, such as head, shoulders, back, chest, front and rear sides of buttock, knee and thigh, the sonar subsystem may deploy a plurality of sonars, and they shall coexist without interfering with one another. To achieve this, the sonars use a common reference clock generated by a reference clock generator 51. In the exemplary embodiment, the sonar subsystem generate N transmitted signals by a signal generator 52, and they are fed to N transmit (Tx) transducers, namely, "Tx transducer 1" 53, ... , "Tx transducer N" 53N. Since using a common clock, the N signals are synchronized with each other. Further, in the exemplary embodiment, M receiving (Rx) transducers are deployed at various parts of the user body (to be detailed hereinafter), they are, respectively, "Rx transducer 1" 54, ... , "Rx transducer M" 54M. All the M received signals as well as the N transmitted signals are fed to a sonar signal processor 55 for processing, detecting and predicting whether there exist a dangerous object to hit any protected parts of the user body shortly, i.e., relative velocity towards user body higher than a safe threshold and distance shorter than a safe threshold. The velocity threshold is determined by how much momentum a body can bear with, when being hit. Given a "reaction time" (for detection and airbag inflation plus some guard time), the distance threshold may be determined by the detected relative velocity multiplied by the reaction time. Alternatively, computing the "time to hit" as the detected distance divided by the detected relative velocity, and use it as a measure to compare with a safe time threshold. The overall processing may be partially accomplished by the controller 42 (not shown), and the sonar signal processor 55 sends its (partially) processed results to the controller 42 by output D 56, and then the controller 42 makes the final decision to inflate selected airbags.

Figure 8:
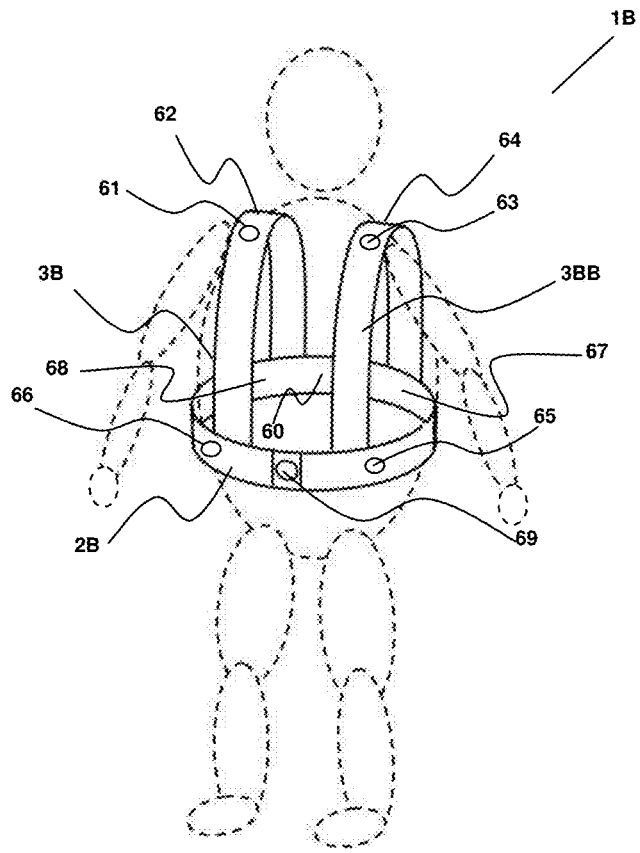
FIG. 8 is an exemplary deployment of the sonar transducers for one of the embodiments presented in FIG. 1.

FIG. 8 is an exemplary deployment of the sonar transducers for one of the embodiments presented in FIG. 1. In order to reliably detect dangerous objects towards the head, shoulders and upper trunk of the user, preferably four Rx transducers are to be deployed, at front and rear sides of the right and left shoulder belts 3B, 3BB, marked as 61, 62, 63, 64. In order to reliably detect any dangerous objects towards the middle and lower parts of trunk and buttock, knee and thigh, another four Rx transducers are preferably to be deployed, at front left and right sides and rear left and right sides of the waist belt 2B, marked as 65, 66, 67, and 68. The four front Rx transducers 61, 63, 65, 66, may share a single Tx transducer source emitted at a preferred position marked as 69, around the front center of the waist belt 2B. The four rear Rx transducers 62, 64, 67, 68 may share a single Tx transducer source emitted at a preferred position marked as 60, around the rear center of the waist belt 2B.

People skilled in the art would understand that, not only the N sonars wearing by the same user (in the example of FIG. 8, N is 8), but also sonars on surrounding people who wear similar airbag devices need to avoid interference with one another. Besides, in nature there may exist some sources producing sound in ultrasound frequency. To avoid interference, preferably the signal generator 52 produces sonar signals using frequency hopping technique that hops the transmitting signal in frequency by random or pseudorandom sequences. People skilled in the art would also understand that, comparing with conventional sonar or sonar for military or navigation purposes, the sonar system 43 for wearable airbag control does not need to have sharp beam for detecting object angles in space.

Falling is a dangerous condition that causes a lot of bodily injuries. Accurately detecting falling of a user body will provide high confidence in making airbag inflation decisions. In static condition, falling happens when the gravity vector from center of mass of a human body is pointing outside the supporting base of the body, usually the outer contour of the two feet when standing. The direction of the gravity can be obtained from 3-dimensional accelerometers (gravimeters), preferably by averaging over readings from more than one accelerometers. These accelerometers are preferably mounted on the waist belt in the front and back sides respectively. A human body's center of mass can be calculated by segmentation method, and since the body posture is changing over time, accurately computing the relative positions of the body segments is the key for the center of mass calculation and for the supporting base calculation.

Figure 9:
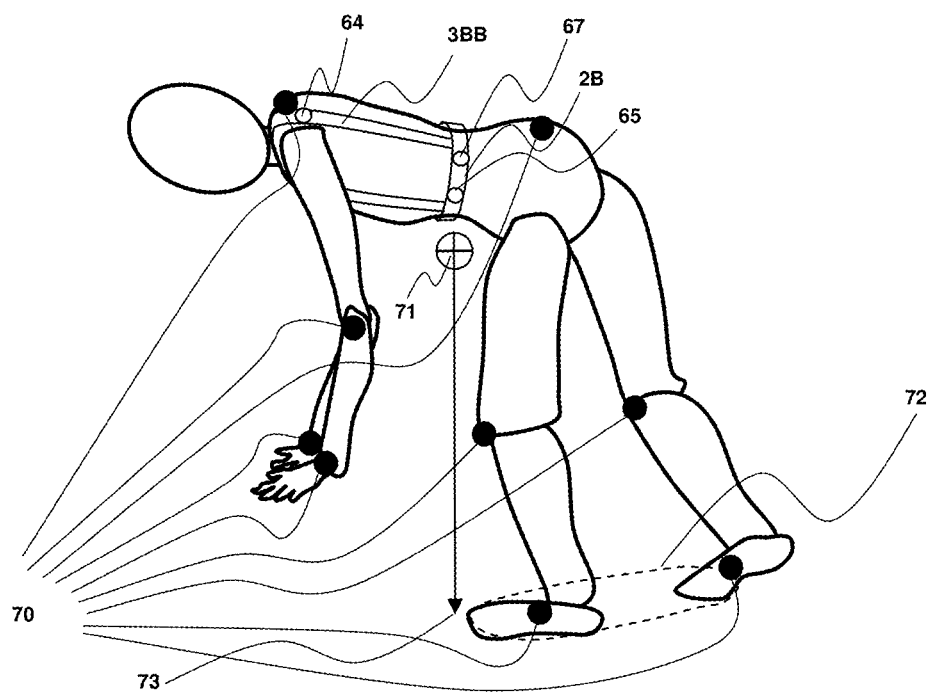
FIG. 9 illustrates a method of falling detection through 3-dimensional (3D) body posture determination using ultrasound trilateration.

FIG. 9 illustrates a method of falling detection through 3-dimensional (3D) body posture determination using ultrasound trilateration. In the abstracted diagram, a person wears an airbag device with waist belt 2B and shoulder belts (one is visible as marked 3BB). On the airbag device, a plurality of Rx ultrasound sonar transducers are mounted. For example, in the embodiment of FIG. 8, eight Rx transducers were recommended. In the drawing three Rx transducers are visible and they are marked as 65, 67, 64. For purpose of 3D body posture determination, using all these eight Rx transducers is good for performance, but not absolutely necessary. Using the four on the waist belt will work. In the figure, it also shows a number "signal tag" devices 70 that are placed on selected important points of body segments to mark the shape of the body posture in 3D. These signal tag devices are active signal generators that spontaneously transmit a time mark signal (e.g., each of the signal tags may transmit a distinct or identical time mark signal repeatedly), or the signal tags may be active "echoers" which transmit a time mark signal in response to a second time mark signal, e.g., from a designated Tx transducer of ultrasound sonar (e.g. 69 in FIG. 8, not shown in FIG. 9) or from the wireless transceiver 46 as in FIG. 6 or from a light emitter such as an inferred emitter (not shown in drawings). In one embodiment the signal tags identify a designed second time mark in the received signal, and then transmit out a signal with a new time marker having a predetermined (or calibrated known) delay from its received time marker (as referred to as "second time mark"). This way, by measuring the time mark delays or delay differences received by the plurality of Rx transducers (e.g., 65, 67, 64 and others not shown in drawing), a processor in the controller 42 (not shown in FIG. 9) is able to calculate the positions of the individual signal tag devices 70 in 3D using trilateration techniques, and obtain the 3D posture shape of the body segments relative to the transducers.

Through the 3D posture shape and estimated weights of body segments, the center of mass position 71 of the body can be calculated. In this example, the center of mass 71 is outside of the physical body. Also, the supporting base footprint 72 can also be obtained, as denoted in dashed line. If the projected point on ground 73 of the gravity vector from the overall body center of mass 71 is significantly outside the supporting base footprint 72, the user body is determined to be falling (out of balance); if the projected point 73 is steadily inside the contour of the supporting base footprint 72, the user body is in balance; if the projected point 73 is close to the contour of the supporting base footprint 72, the user body's balance condition is marginal and may be risky. Note that a transition to sitting is a special "falling" condition that needs to be detected and treated separately. With sonar and sensors as well as the method described hereinabove, people skilled in the art will be able to handle it, and thus will not be discussed in further detail. The signal tags may be placed at or closed to a joint between two body segments to mark a position of the joint, or directly mark a position of a mass center of a segment or a geometry center of a segment. Since the signal tags can only be placed outside a body segment, while a mass or geometry center is inside the body tissues, in the case of torso, for example, the inside position of mass center or geometry center of the torso has quite a distance to the outside signal tag position in 3D, we may use multiple signal tags around a segment to mark a position inside, for example using the geometry center of three signal tags outside the torso to mark an accurate position of the mass center of torso inside. Signal tags can also be placed to mark the positions of supporting base contour by place them at edges of shoes and around buttock.

The time mark in the ultrasound sonar signal can be implemented in a number of ways, e.g., a transition edge of frequency hopping, a pulse edge modulated onto the ultrasound signal, a designated code sequence, etc. In a preferred embodiment, the transition edge of frequency hopping is used.

Preferably the signal tag devices are made small in size, for example as little as or smaller than a button, so that they can be easily attached on clothing without causing any inconvenience.

In using trilateration techniques, constraint conditions (such as the distance between two signal tags attached on a single rigid body segment is fixed and known) and over determination using extra measurements (such as extra measurements from more than necessary transducers) may be used to improve accuracy of the posture determination. Such techniques are well known to ones skilled in the art of GPS positioning, and will not be described in detail.

The terminology of "echo" is used in a broad sense in the description of features of the signal tags. It does not necessarily mean transmit back a signal identical to its received signal. The echoed signal may be different, such as different in frequency, or even different in nature (such as using ultrasound to echo a time mark received in radio signal, etc.). Alternative embodiments are possible, for example, embodiment 1: using ultrasound for both downlink (from sonar Tx transducer to signal tags) and uplink (from signal tags to sonar Rx transducers); embodiment 2: use radio for downlink (from a radio transceiver to signal tags) and use ultrasound for uplink (from signal tags to sonar Rx transducers); embodiment 3: use ultrasound for downlink (from 3 or more sonar Tx transducers to signal tags) and radio as uplink (from signal tags to a radio transceiver). In principle all these three embodiments work, but complexity differs, some needs more complicated signal tags, some needs more complicated math calculation. Light signal such as inferred signal may also be used on a link.

Figure 10:
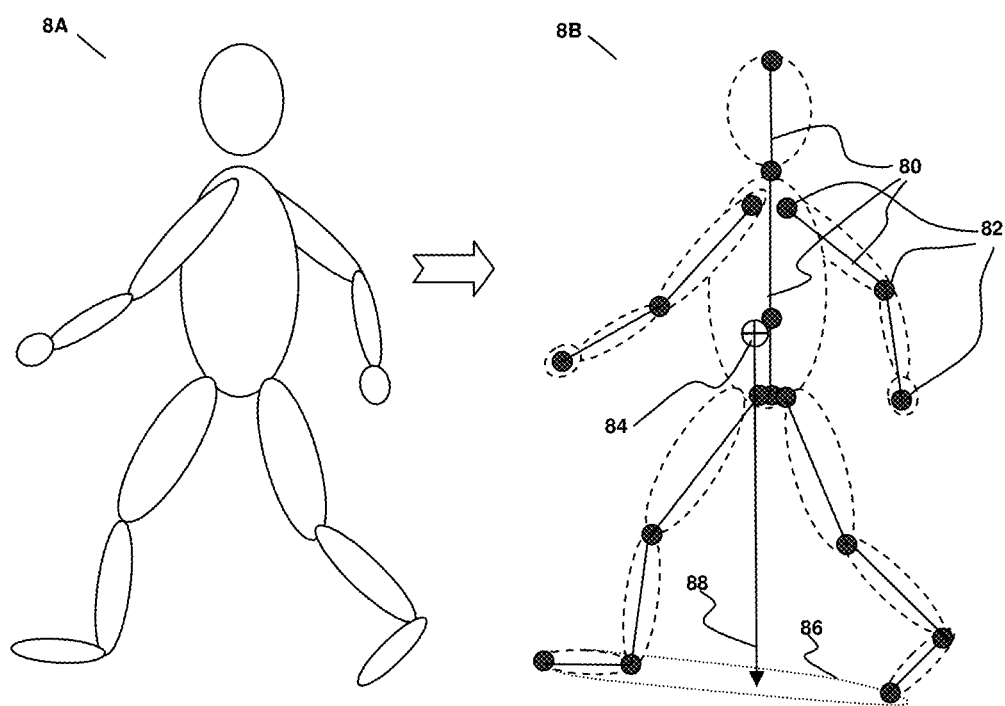
FIG. 10 illustrates a method of falling detection through 3-dimensional (3D) body posture determination using image recognition of body segments.

FIG. 10 illustrates a method of falling detection through 3-dimensional (3D) body posture determination using image recognition of body segments. In this exemplary drawing, a raw image 8A of a protected user taken by an image sensor is processed in the controller 42 (as in FIG. 6) by an image processing module in it, in the drawing, relative positions of the body segments 8B are recognized and marked as solid lines 80 and the joints connecting the body segments are recognized and shown as black dots 82. Each of the body segments is rigid or semi-rigid, whose mass center and weight can be estimated fairly accurately. Once the relative positions of each body segment is determined, mass center position 84 of the overall body can be calculated. With proper view angles of one or a plurality of image sensors (e.g. still picture cameras and/or video cameras), real-time images of the human body can be taken and processed to recognize the body segments within each individual 2-dimensional (2D) image. The lengths of body segments of a user under protection are known or can be estimated through distance and angle measurements in the image and/or through the image sensor (e.g., using auto focus and related techniques of a camera, which are known to the ordinary skilled in the art). Since the segments are connected with one another through joints, the relative position of the segments are not free in the 3D space but are constrained, for example a knee should be located only on a sphere surface centered at the hip joint with radius of the length of the thigh, subject to the hip joint movement limits. Together with the knowledge of the constraints of the body segments, a 2D image with good view angle will enable us to calculate the relative positions of the body segments in 3D (e.g., represented by positions of joints connecting the segments). When more than one image sensors are available, if the view angles and relative position of each of the image sensors are determined, then the images obtained from the more than one image sensors can be used jointly to compute and/or improve the accuracy in computing the relative positions of the body segments in 3D. Similar to the techniques described with FIG. 9, with determined direction of gravity 88, position of overall body mass center 84 as well as supporting base footprint 86, we are able to determine if the user is falling by verifying whether the mass center is pointing, in the direction of gravity, outside the supporting base footprint. The direction of gravity can be measured by an accelerometer sensor, can also be derived from the images, for example, from image of floor, the gravity direction is vertical to the plane of floor.

In an alternative embodiments, since the density of human body segments is nearly even and nearly symmetrical, the position of a geometrical center of a human body or body segment is a good approximation to a mass center of the human body or body segment, a geometrical center as can be estimated in an image of human body may also be used for falling detection purpose, together with determined direction of gravity and relative position of supporting base foot print. Furthermore, direct detection of abnormal movement of a human body segment, e.g., movement of head, torso, and/or hip towards ground or significantly away from above the supporting base of feet, is also usable as means to detect falling, as seen in a real-time image of human body.

Figure 11:
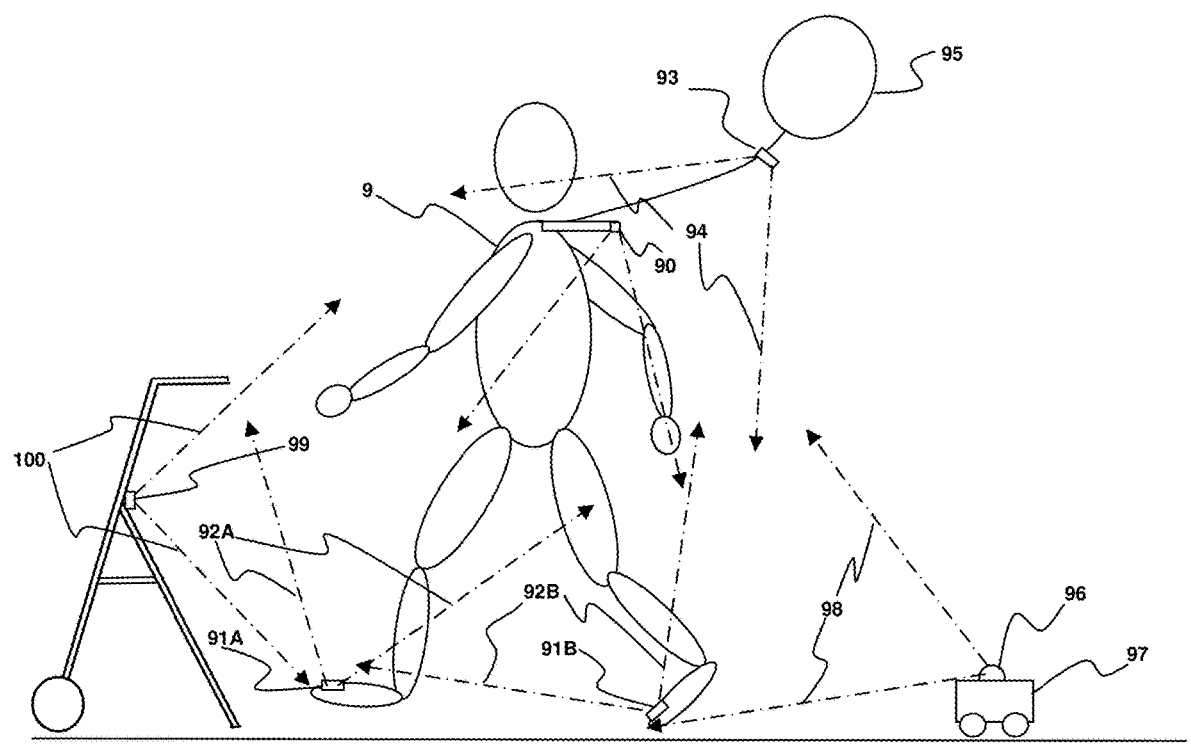
FIG. 11 illustrates a few examples of image sensor placement and view angles towards a user for use in controlling the airbag device.

Embodiments of fall detection using real-time image of user require good view angle and good view scope of the user under protection. FIG. 11 illustrates a few examples of image sensor placement and view angles towards a user for use in controlling the airbag device. In one of the preferred embodiments, the image sensor(s) 91A and/or 91B is/are installed on upper side of shoes worn by the user, and are coupled with the controller 42 (as in FIG. 6) through wired or wireless means. Their view angles 92A, 92B are upward with as much coverage as possible over major body segments of the user 9. In order to obtain image sensor orientation information relative to gravity direction, accelerometer sensor(s) is/are preferably installed on one or both image sensor(s) 91A and/or 91B. The accelerometer sensor(s) also help(s) to link the images obtained by two image sensors 91A and 91B on two shoes together for joint detection. Preferably the view angle and/or view scope of the image sensor(s) 91A and/or 91B can be controlled in real-time by controller 42 (as in FIG. 6) by mechanical and/or electronic means. One of the preferred embodiment is to pre-install multiple cameras in distinct view angles and select one(s) with optimal view for detection. Image sensor may also be attached to the user through a rigid or semi-rigid support, one example is shown as 90 in the drawing.

In another preferred embodiment, the image sensor is installed on an observing device in the air, such as an observing unit 93 hanging on a balloon 95 tethered with the user 9 under protection, or installed on a drone (not shown in the drawing) hovering around the user 9. Alternatively the image sensor 96, 99 may be installed on a mobile observing device 97 that automatically follows the user 9 or worn on a trained animal such as a dog (not shown in drawing) that follows the user 9, or installed on a walker, rollator or the like that moves in front of the user, etc. An image sensor installed on a platform not physically attached to the user under protection, such as a drone, a mobile observing device, a walker, a rollator or other types of platforms, or worn on a trained animal must identify the right person as protecting target so that the view angles (e.g., 94, 98, 100) are towards the right person to take images, among possibly a crowd of people. The protected user 9 may wear some special identity markers to help the image sensor to identify the right target, such as a bar code, a 2D bar code or other types visible symbol, or wear a light emitter such as an inferred light emitter, which may emit a code sequence or other identity signal repeatedly or in response to a request signal, that can be detected by the image sensor.

Preferably at least one image sensor is able to see relative positions of major body segments as well as the supporting base of feet at least partially in a single image so that from an image the balance conditions can be determined. Alternatively, as in the embodiment that the image sensors are installed on shoes, although the supporting base footprint is not visible in an image taken by the image sensor, the positions of body segments in an image relative to the supporting base is still known from the image, since the supporting base as established by feet is simply behind the image sensors. If not able directly to see the supporting base of feet in an image, seeing the legs would sill allow to estimate the supporting base fairly accurately as the legs below knees are straight and the position ranges of feet relative to the legs are known for a given user. Additional information collected from sensors placed on shoes may also be used to increase accuracy, for example, pressure sensors placed on soles of shoes may report which part of a foot is providing support to the weight of user body. Relative positions of feet may also be measured using the signal tag techniques as described hereinabove with FIG. 9.

Optionally, in order for easy and accurate recognition of body segments in an image, a plurality of markers distinctly visible to the image sensor(s) can be placed on selected important points of body segments to mark the shape of the body posture, similar to those signal tags 70 as shown in FIG. 9. These markers may be objects with known shape or pattern or color on them (such as a bar code, a 2D bar code or other image patterns), or may be active light emitters such as inferred light emitters, which may emit human-invisible or visible light constantly, or repeatedly with an on-off pattern, or with distinct codes or timing specific to a marked body position of a user. Other variations in embodiments may also be used. The markers may be placed at or closed to a joint between two body segments, or mark the position of a mass center of a segment or a geometry center of a segment. Since the marks can only be placed outside a body segment, while a mass or geometry center is inside the body tissues, in the case of torso, for example, the inside position of mass center or geometry center has quite a distance to the outside marker position in 3D, we may use multiple markers around a segment to mark a position inside, for example using the geometry center of three markers outside the torso to mark an accurate position of the mass center of torso inside.

Relative positions and orientation of the image sensors may be estimate through images of the user, for example, distance to a segment of user body may be estimated based on image size of the body segment of the user, angle relation of the sensor view relative to body segments. Sensors installed on each of the image sensors may also provide information to estimate the relative positions and orientation of the image sensors, such as accelerators may measure the orientation relative to earth gravity, magnetic sensors may sense the earth magnetic field and provide orientation relative to earth magnetic field. If a signal tag as described hereinabove with FIG. 9 is placed on an image sensor, the technique described with FIG. 9 can be used to determine relative position of the image sensor based on timing of time mark signals, regardless the image sensor is placed on or off the user body. Camera auto focus techniques that are known in the art can also be used to determine distance of an image sensor to the focused object (e.g., a body segment of the user), in conjunction with estimation through a size and angle of a body segment as seen in an image.

In an alternative embodiment, an airbag device may be mounted on an mobile platform that moves around the protected user, e.g., a platform automatically follows a user and when detecting a dangerous falling condition, an airbag device is lunched out from the mobile platform, for example, popping out from a mobile platform by a released spring, or pushed out from a mobile platform by a rod, etc. The airbag device is lunched out to a position between the falling user and the ground so that the airbag will be inflated to effectively absorb the impact energy to protect the user from being hurt. The airbag inflator in the airbag device is coupled with the controller either through wire or wirelessly means to accept an ignition signal. If the mobile platform is a device that follows the user automatically, such as a vehicle or a robot, preferably they move beside the user so that when the user falling forward, it will still be able to deploy the airbag device in front of the user, while not in way of the walking user.

In alternative embodiments, the airbag device may be embedded in a garment such as a vest, a jacket or a coat. Such embodiments are suitable for mild and cold environment conditions other than summer outdoor environment.

The inflators may also use technologies other than propellant based chemical reactions, such as compressed air.

Certain terms are used to refer to particular components. As one skilled in the art will appreciate, people may refer to a component by different names. It is not intended to distinguish between components that differ in name but not in function. For example, in the specification and claims, the terminology "sonar" is used, to refer to detecting and ranging devices based on reflected acoustic wave from objects, where the wave used is preferably ultrasound, i.e., to refer to an ultrasonic motion/proximity sensor; the terminology "airbag" may be referred to as "airbag cushion" or "air cushion". The word "hit" in the specification and claims always appears as "an object hits the body", in fact, what matters is they hit each other. In real world it may be "the body hits an object", e.g., falling is that the body hits the ground. It should be understood that throughout this application, "A hits B" always means A and B hits each other without distinguishing subject and object.

The terms "including" and "comprising" are used in an open-ended fashion, and thus should be interpreted to mean "including, but not limited to". The terms "example" and "exemplary" are used simply to identify instances for illustrative purposes and should not be interpreted as limiting the scope of the invention to the stated instances.

Also, the term "couple" in any form is intended to mean either a direct connection or indirect connection through other devices and connections.

It should be understood that various modifications can be made to the embodiments described and illustrated herein, without departing from the invention, the scope of which is defined in the appended claims.

I claim:

1. An airbag device for preventing bodily injury of a user, comprising:
   at least one inflatable airbag, mounted on the airbag device for absorbing energy when the user is falling and about to hit the floor or an object;
   at least one airbag inflator, for accepting an igniting signal to inflate the at least one inflatable airbag;
   at least one image sensor, for taking images in real-time of body segments of the user and objects surrounding the user;
   at least one of an accelerometer and a gyro sensor, installed on the at least one image sensor, for sensing information related to an orientation and/or a position of the at least one imaging sensor; and
   a controller, coupled with the at least one airbag inflator, the at least one image sensor, and said at least one of the accelerometer and the gyro sensor, whereby the controller is operable to
   determine a status indicating whether the user is falling based, at least in part, on information extracted from the images,
   make a decision of airbag inflation based, at least in part, on the determined status of falling, and
   send, upon positive decision of airbag inflation, an igniting signal to the at least one airbag inflator.

2. An airbag device for preventing bodily injury of a user, comprising:
   at least one inflatable airbag, mounted on the airbag device for absorbing energy when the user is falling and about to hit the floor or an object;
   at least one airbag inflator, for accepting an igniting signal to inflate the at least one inflatable airbag;
   at least one image sensor, for taking images in real-time of body segments of the user and objects surrounding the user;
   a controller, coupled with the at least one airbag inflator, and the at least one image sensor,
whereby the controller is operable to determine at least one of:
   a relative position and orientation in 3-dimensions of the image sensor, based, at least in part, on the information extracted from the images;
   a relative direction of gravity based on information extracted from the images;
   relative positions in 3-dimensions of the body segments of the user, based, at least in part, on information extracted from the images and constraints of connections between the segments;
   relative positions in 3-dimensions of center of mass of each of the body segments of the user, based, at least in part, on information extracted from the images and constraints of connections between the segments;
   a relative position of overall center of mass of the user body, based, at least in part, on relative positions of the center of mass and weights of each of the body segments of the user;
   a relative position in 3-dimensions of overall center of mass of the user body, based, at least in part, on a position of geometry center of overall body of the user or positions of geometry center of each of the body segments of the user;
   a status indicating the user is sitting or standing, based, at least in part, on information extracted from the images;
   a relative position of supporting base footprint, based on relative positions of feet when determined standing, and based on relative positions of feet and buttock when determined sitting; and
   a status indicating whether the user is falling based, at least in part, on relative position of an overall center of mass of the user body, relative position of the supporting base footprint, and a direction of the gravity;
   a decision of airbag inflation based, at least in part, on the determined status of falling; and
   sending, upon positive decision of airbag inflation, an igniting signal to the at least one airbag inflator.

3. The airbag device of claim 2 further including at least one additional sensor, placed at predetermined at least one location on the airbag device or on the body of the user, coupled with the controller, for collecting information for controlling the airbag device.

4. The airbag device of claim 3, wherein said at least one additional sensor includes at least one of:
- at least one accelerometer;
- at least one gravimeter;
- at least one gyro sensor;
- at least one muscle electrical potential sensor;
- at least one pressure sensor;
- at least one microphone;
- at least one vibration sensor; and
- at least one infrared sensor.

5. The airbag device of claim 4, wherein at least one of the at least one accelerometer and the at least one gyro sensor is installed on the image sensor.

6. The airbag device of claim 5, wherein the controller is further operable to determine at least one of:
- a relative position and orientation in 3-dimensions of the image sensor, based, at least in part, on the information extracted from the images and a measurement from the accelerometer and/or the gyro sensor installed on the image sensor;
- a relative direction of gravity based, at least in part, on at least one of information extracted from the images and a measurement from the accelerometer installed on the image sensor and/or the accelerometer on the airbag device or on the body of the user; and
- a status indicating whether the user is falling based, at least in part, on relative position of an overall center of mass of the user body, relative position of the supporting base footprint, a direction of the gravity measured by the accelerometer.

7. The airbag device of claim 6, wherein said operable to determine and said further operable to determine is based jointly on images obtained from two or more than two image sensors.

8. The airbag device of claim 4 further including a sonar subsystem with at least one sonar transmitting transducer and a plurality of sonar receiving transducers which are placed at predetermined distinct locations on the airbag device or on the body of the user, coupled with the controller, for collecting information for controlling the airbag device.

9. The airbag device of claim 8, wherein the sonar makes use of Doppler effect.

10. The airbag device of claim 8, wherein the at least one sonar transmits ultrasound signals with frequency hopping.

11. The airbag device of claim 8, wherein the controller is further operable to determine whether or not to inflate the at least one airbag based, at least in part, on a detected velocity and a distance of a surrounding object towards the user reported by the sonar.

12. The airbag device of claim 8 further including a plurality of signal tags, adapted to be placed at a plurality of distinct locations on the user body and/or on the at least one image sensor, configured to transmit, from each of the plurality of signal tags, a time mark signal either spontaneously or in response to a second time mark signal.

13. The airbag device of claim 12, wherein the plurality of signal tags are placed at at least one of:
- a position at or close to a joint between two segments of the user body;
- a position at or close to a center of mass of a body segment of the user;
- a position at or close to a geometry center of a body segment of the user; and
- a position at or close to an edge of foot supporting base; and
- a position at or close to an edge of buttock supporting base.

14. The airbag device of claim 13, wherein the controller is further operable to determine at least one of:
- a relative position in 3-dimensions of the image sensor that is co-located with one of the signal tags, based, at least in part, on a timing of the time mark signal from the signal tag co-located with the image sensor and measured from at least three of the plurality of sonar receiving transducers;
- relative positions in 3-dimensions of the signal tags based, at least in part, on a timing of the time mark signals from the signal tags and measured from at least three of the plurality of sonar receiving transducers;
- relative positions of body segments of the user in 3-dimensions, based on at least one of a timing of the time mark signals measured from at least three of the plurality of sonar receiving transducers and information extracted from the images;
- relative positions in 3-dimensions of center of mass of each of the body segments of the user, based on at least one of a timing of the time mark signals measured from at least three of the plurality of sonar receiving transducers and information extracted from the images;
- relative positions in 3-dimensions of geometry center of each of the body segments of the user, based on at least one of a timing of the time mark signals measured from at least three of the plurality of sonar receiving transducers and information extracted from the images;
- a relative position of overall center of mass of the user body, based on relative positions of the center of mass and weights of each of the body segments of the user;
- a relative position of overall center of mass of the user body, based on relative positions of the geometry center of each of the body segments of the user;
- a relative position of overall center of mass of the user body, based, at least in part, on relative positions of geometry center of each of the body segments of the user;
- a status indicating the user is sitting or standing, based, at least in part, on at least one of a timing of the time mark signals measured from at least three of the plurality of sonar receiving transducers and information extracted from the images;
- a relative position of supporting base footprint, based on relative positions of feet or signal tags marking the feet supporting base when determined standing, and based on relative positions of feet and buttock or signal tags marking the feet and buttock supporting base when determined sitting; and
- a status indicating whether the user is falling based, at least in part, on determined relative position of the overall center of mass of the user body, relative position of the supporting base footprint, a measured direction of the gravity.

15. The airbag device of claim 8 further including at least one wireless transceiver for at least one of:
- reporting an airbag inflating incident to at least one predetermined terminal device;
- providing communication means between service staff and the user or a person at the user's location;
- sending event log data to a service center;
- transferring data between the controller and the at least one image sensors;
- transferring data between the controller and the at least one of the additional sensors;

transferring signaling between the controller and at least one of the additional sensors;
transferring data between the controller and the sonar subsystem;
transferring signaling between the controller and the sonar subsystem;
transferring signaling between the controller and at least one airbag inflators;
downloading software upgrades onto the airbag device;
communicating with cellular basestations for location determination; and
receiving global positioning satellite signals for location determination.

16. The airbag device of claim 4 further including at least one wireless transceiver for at least one of:
reporting an airbag inflating incident to at least one predetermined terminal device;
providing communication means between service staff and the user or a person at the user's location;
sending event log data to a service center;
transferring data between the controller and the at least one image sensors;
transferring data between the controller and the at least one of the additional sensors;
transferring signaling between the controller and at least one of the additional sensors;
transferring signaling between the controller and at least one airbag inflators;
downloading software upgrades onto the airbag device;
communicating with cellular basestations for location determination; and
receiving global positioning satellite signals for location determination.

17. The airbag device of claim 4, wherein said at least one image sensor is at least one of:
a still picture camera;
a video camera;
a still picture camera capable of taking images in infrared band;
a video camera capable of taking images in infrared band;
a stereoscopic camera; and
a camera capable of sensing distances from objects.

18. An airbag protection system for preventing bodily injury of a user, comprising:
at least one mobile platform that moves accompanying with the user;
at least one inflatable airbag device, stored on the at least one mobile platform, for being deployed and inflated on a floor and absorbing impact energy when the user falls towards the floor;
at least one airbag device launcher, mounted on the at least one mobile platform, for popping out the inflatable airbag device on the floor;
at least one airbag inflator, for accepting an igniting signal to inflate the at least one inflatable airbag device;
at least one image sensor, installed on the mobile platform or attached to the user, for taking images of body segments of the user and objects surrounding the user in real-time; and
a controller, coupled with the at least one airbag device launcher, the at least one airbag inflator, and the at least one image sensor, whereby the controller is operable to
determine a status indicating whether the user is falling based, at last in part, on information extracted from real-time images of the user;
send launching signals to the at least one airbag device launcher; and
send igniting signal to an airbag inflator associated with the inflatable airbag device being launched.

19. The airbag protection system of claim 18, further including at least one sensor, attached to the user and coupled with the controller, for collecting information to control the airbag protection system.

20. The airbag protection system of claim 19, further including at least one wireless transceiver for at least one of:
reporting an airbag inflating incident to at least one predetermined terminal device;
providing communication means between service staff and the user or a person at the user's location;
sending event log data to a service center;
transferring data between the controller and the at least one image sensors;
transferring data between the controller and the at least one sensor;
transferring signaling between the controller and the at least one sensor;
transferring signaling between the controller and at least one airbag inflator;
downloading software upgrades onto the airbag protection system;
communicating with cellular basestations for location determination; and
receiving global positioning satellite signals for location determination.

* * * * *